United States Patent
Cumming

(10) Patent No.: US 9,629,711 B2
(45) Date of Patent: *Apr. 25, 2017

(54) INTRAOCULAR LENS

(71) Applicant: James Stuart Cumming, Laguna Beach, CA (US)

(72) Inventor: James Stuart Cumming, Laguna Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/140,940

(22) Filed: Apr. 28, 2016

(65) Prior Publication Data

US 2016/0235522 A1    Aug. 18, 2016

Related U.S. Application Data

(63) Continuation of application No. 14/584,188, filed on Dec. 29, 2014, which is a continuation-in-part of application No. 14/257,933, filed on Apr. 21, 2014, now Pat. No. 8,351,825, which is a continuation-in-part of application No. 14/143,612, filed on Dec. 30, 2013, now abandoned.

(60) Provisional application No. 61/921,782, filed on Dec. 30, 2013.

(51) Int. Cl.
    *A61F 2/16*    (2006.01)

(52) U.S. Cl.
    CPC .... *A61F 2/1613* (2013.01); *A61F 2002/1689* (2013.01); *A61F 2002/169053* (2015.04)

(58) Field of Classification Search
    CPC ................ A61F 2/1629; A61F 2/1648; A61F 2002/1689; A61F 2002/1681
    See application file for complete search history.

(56) References Cited

U.S. PATENT DOCUMENTS

| 2,834,023 A | 5/1958 | Wolfgang |
| 4,073,014 A | 2/1978 | Poler |
| 4,118,808 A | 10/1978 | Poler |
| 4,122,556 A | 10/1978 | Poler |

(Continued)

FOREIGN PATENT DOCUMENTS

| CA | 2110184 A1 | 12/1992 |
| CH | 681687 | 5/1993 |

(Continued)

OTHER PUBLICATIONS

Dykstra, M., et al. Biological Electron Microscopy: Theory, Techniques, and Troubleshooting, 2003, p. 81.

(Continued)

*Primary Examiner* — David H Willse
*Assistant Examiner* — Tiffany Shipmon
(74) *Attorney, Agent, or Firm* — Sheppard, Mullin, Richter & Hampton LLP

(57) ABSTRACT

An intraocular lens including a flexible optic and at least one rigid plate haptic connected to the optic. The at least one rigid plate haptic can include a rigid structure. The at least one rigid plate haptic can be resistant to bending from pressure exerted on a distal end of the at least one haptic by contraction of the ciliary muscle. The intraocular lens can be a non-accommodating IOL having a longitudinal length that is fixed and configured to resist deformation by the action of the ciliary muscle. Various embodiments also include accommodating intraocular lenses.

22 Claims, 12 Drawing Sheets

(56) References Cited

U.S. PATENT DOCUMENTS

| | | |
|---|---|---|
| 4,159,546 A | 7/1979 | Shearing |
| 4,168,547 A | 9/1979 | Konstantinov et al. |
| 4,173,798 A | 11/1979 | Welsh |
| 4,174,543 A | 11/1979 | Kelman |
| 4,206,518 A | 6/1980 | Jardon et al. |
| 4,244,060 A | 1/1981 | Hoffer |
| 4,254,509 A | 3/1981 | Tennant |
| 4,277,851 A | 7/1981 | Choyce et al. |
| 4,298,995 A | 11/1981 | Poler |
| 4,304,012 A | 12/1981 | Richard |
| 4,409,690 A | 10/1983 | Gess |
| 4,409,691 A | 10/1983 | Levy |
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,629,462 A | 12/1986 | Feaster |
| 4,648,878 A | 3/1987 | Kelman |
| 4,664,665 A | 5/1987 | Reuss et al. |
| 4,664,666 A | 5/1987 | Barrett |
| 4,673,406 A | 6/1987 | Schlegel |
| 4,681,102 A | 7/1987 | Bartell |
| 4,704,123 A | 11/1987 | Smith |
| 4,710,195 A | 12/1987 | Glovinazzo |
| 4,718,904 A | 1/1988 | Thornton |
| 4,737,322 A | 4/1988 | Bruns et al. |
| 4,738,680 A | 4/1988 | Herman |
| 4,743,254 A | 5/1988 | Davenport |
| 4,753,655 A | 6/1988 | Hecht |
| 4,759,761 A | 7/1988 | Portnoy |
| 4,763,650 A | 8/1988 | Hauser |
| 4,765,329 A | 8/1988 | Cumming et al. |
| 4,769,033 A | 9/1988 | Nordan |
| 4,769,035 A | 9/1988 | Kelman |
| 4,778,463 A | 10/1988 | Hetland |
| 4,781,719 A | 11/1988 | Kelman |
| 4,790,847 A | 12/1988 | Woods |
| 4,793,344 A | 12/1988 | Cumming et al. |
| 4,813,955 A | 3/1989 | Achatz et al. |
| 4,816,030 A | 3/1989 | Robinson |
| 4,840,627 A | 6/1989 | Blumenthal |
| 4,842,601 A | 6/1989 | Smith |
| 4,846,833 A | 7/1989 | Cumming |
| 4,862,885 A | 9/1989 | Cumming |
| 4,868,251 A | 9/1989 | Reich et al. |
| 4,880,427 A | 11/1989 | Anis |
| 4,888,012 A | 12/1989 | Horn et al. |
| 4,892,543 A | 1/1990 | Turley |
| 4,919,130 A | 4/1990 | Stoy et al. |
| 4,932,966 A | 6/1990 | Christie et al. |
| 4,932,968 A | 6/1990 | Caldwell et al. |
| 4,932,970 A | 6/1990 | Portney |
| 4,936,850 A | 6/1990 | Barrett |
| 4,963,148 A | 10/1990 | Sulc et al. |
| 4,969,897 A | 11/1990 | Kalb |
| 4,976,716 A | 12/1990 | Cumming |
| 4,978,354 A | 12/1990 | Van Gent |
| 4,994,082 A | 2/1991 | Richards et al. |
| 5,047,051 A | 9/1991 | Cumming |
| 5,066,297 A | 11/1991 | Cumming |
| 5,078,742 A | 1/1992 | Dahan |
| 5,141,507 A | 8/1992 | Parekh |
| 5,152,788 A | 10/1992 | Isaacson et al. |
| 5,152,789 A | 10/1992 | Willis |
| 5,171,319 A | 12/1992 | Keates et al. |
| 5,171,320 A | 12/1992 | Nishi |
| 5,180,390 A | 1/1993 | Drews |
| 5,217,490 A | 6/1993 | Sayano et al. |
| 5,275,604 A | 1/1994 | Rheinish et al. |
| 5,275,623 A | 1/1994 | Sarfarazi |
| 5,275,624 A | 1/1994 | Hara et al. |
| 5,290,310 A | 3/1994 | Makower et al. |
| 5,304,182 A | 4/1994 | Rheinish et al. |
| 5,324,306 A | 6/1994 | Makower et al. |
| 5,326,347 A | 7/1994 | Cumming |
| 5,366,502 A | 11/1994 | Patel |
| 5,376,115 A | 12/1994 | Jansen |
| 5,425,734 A | 6/1995 | Blake |
| 5,443,506 A | 8/1995 | Garabet |
| 5,474,562 A | 12/1995 | Orchowski et al. |
| 5,476,514 A | 12/1995 | Cumming |
| 5,489,302 A | 2/1996 | Skottun |
| 5,496,366 A | 3/1996 | Cumming |
| 5,522,891 A | 6/1996 | Klaas |
| 5,562,731 A | 10/1996 | Cumming |
| 5,578,042 A | 11/1996 | Cumming |
| 5,578,078 A | 11/1996 | Nakajima et al. |
| 5,607,472 A | 3/1997 | Thompson |
| 5,611,968 A | 3/1997 | Grisoni et al. |
| 5,674,282 A | 10/1997 | Cumming |
| 5,686,414 A | 11/1997 | Scannon |
| 5,699,142 A | 12/1997 | Lee et al. |
| 5,716,403 A | 2/1998 | Tran et al. |
| 5,800,532 A | 9/1998 | Lieberman |
| 5,837,156 A | 11/1998 | Cumming |
| 5,843,187 A | 12/1998 | Bayers |
| 5,873,879 A | 2/1999 | Figueroa et al. |
| 5,919,230 A | 7/1999 | Sambursky |
| 5,944,725 A | 8/1999 | Cicenas et al. |
| 5,968,094 A | 10/1999 | Werblin et al. |
| 5,984,914 A | 11/1999 | Cumming |
| 6,007,579 A | 12/1999 | Lipshitz et al. |
| 6,013,101 A | 1/2000 | Israel |
| 6,015,435 A | 1/2000 | Valunin et al. |
| 6,027,531 A | 2/2000 | Tassignon |
| 6,051,024 A | 4/2000 | Cumming |
| 6,066,171 A | 5/2000 | Lipshitz et al. |
| 6,066,172 A | 5/2000 | Huo et al. |
| 6,113,633 A | 9/2000 | Portney |
| 6,129,760 A | 10/2000 | Fedorov et al. |
| 6,161,544 A | 12/2000 | DeVore et al. |
| 6,164,282 A | 12/2000 | Gwon et al. |
| 6,176,878 B1 | 1/2001 | Gwon et al. |
| 6,179,870 B1 | 1/2001 | Sourdille et al. |
| 6,193,750 B1 | 2/2001 | Cumming |
| 6,197,058 B1 | 3/2001 | Portney |
| 6,197,059 B1 | 3/2001 | Cumming |
| 6,217,612 B1 | 4/2001 | Woods |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,409,763 B1 | 6/2002 | Brady |
| 6,413,276 B1 | 7/2002 | Werblin |
| 6,419,697 B1 | 7/2002 | Kelman |
| 6,423,094 B1 | 7/2002 | Sarfarazi |
| 6,443,985 B1 | 9/2002 | Woods |
| 6,451,056 B1 | 9/2002 | Cumming |
| 6,461,384 B1 | 10/2002 | Hoffmann et al. |
| 6,488,708 B2 | 12/2002 | Sarfarazi |
| 6,494,911 B2 | 12/2002 | Cumming |
| 6,497,708 B1 | 12/2002 | Cumming |
| 6,503,275 B1 | 1/2003 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,540,353 B1 | 4/2003 | Dunn |
| 6,558,420 B2 | 5/2003 | Green |
| 6,613,343 B2 | 9/2003 | Dillingham et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,660,035 B1 | 12/2003 | Lang et al. |
| 6,660,036 B2 | 12/2003 | Cumming |
| 6,685,741 B2 | 2/2004 | Landreville et al. |
| 6,695,881 B2 | 2/2004 | Peng et al. |
| 6,749,634 B2 | 6/2004 | Hanna |

(56) References Cited

U.S. PATENT DOCUMENTS

| | | |
|---|---|---|
| 6,767,363 B1 | 7/2004 | Bandhauer et al. |
| 6,849,091 B1 | 2/2005 | Cumming |
| 6,858,040 B2 | 2/2005 | Nguyen et al. |
| 6,881,225 B2 | 4/2005 | Okada |
| 6,884,263 B2 | 4/2005 | Valyunin |
| 6,921,416 B2 | 7/2005 | Khoury |
| 6,926,736 B2 | 8/2005 | Peng |
| 6,969,403 B2 | 11/2005 | Peng |
| 6,972,033 B2 | 12/2005 | McNicholas |
| 7,018,409 B2 | 3/2006 | Glick |
| 7,025,783 B2 | 4/2006 | Brady |
| 7,037,338 B2 | 5/2006 | Nagamoto |
| 7,048,760 B2 | 5/2006 | Cumming |
| 7,097,660 B2 | 8/2006 | Portney |
| 7,125,422 B2 | 10/2006 | Woods et al. |
| 7,150,759 B2 | 12/2006 | Paul et al. |
| 7,150,760 B2 | 12/2006 | Zhang |
| 7,229,475 B2 | 6/2007 | Glazier |
| 7,229,476 B2 | 6/2007 | Azar |
| 7,300,464 B2 | 11/2007 | Tran |
| 7,326,246 B2 | 2/2008 | Brady |
| 7,341,599 B1 | 3/2008 | Peyman |
| 7,435,258 B2 | 10/2008 | Blake |
| 7,435,259 B2 | 10/2008 | Cumming |
| 7,553,327 B2 | 6/2009 | Cumming |
| 7,662,180 B2 | 2/2010 | Paul et al. |
| 7,763,070 B2 | 7/2010 | Cumming |
| 7,837,730 B2 | 11/2010 | Cumming |
| 7,981,155 B2 | 7/2011 | Cumming |
| 7,985,253 B2 | 7/2011 | Cumming |
| 8,038,711 B2 | 10/2011 | Clarke |
| 8,080,056 B2 | 12/2011 | Cumming |
| 8,100,965 B2 | 1/2012 | Cumming et al. |
| 8,109,998 B2 | 2/2012 | Cumming |
| 8,163,015 B2 | 4/2012 | Cumming |
| 8,216,308 B2 | 7/2012 | Blake et al. |
| 8,523,942 B2 | 9/2013 | Cumming |
| 8,734,512 B2 | 5/2014 | Cumming |
| 8,764,823 B2 | 7/2014 | Cumming |
| 2001/0001836 A1 | 5/2001 | Cumming |
| 2002/0120329 A1 | 8/2002 | Lang et al. |
| 2002/0138140 A1 | 9/2002 | Hanna |
| 2003/0060881 A1 | 3/2003 | Glick et al. |
| 2003/0078658 A1 | 4/2003 | Zadno-Azizi |
| 2003/0097177 A1 | 5/2003 | Tran |
| 2003/0109925 A1 | 6/2003 | Ghazizadeh et al. |
| 2003/0135272 A1 | 7/2003 | Brady et al. |
| 2003/0142269 A1 | 7/2003 | Cumming |
| 2003/0171808 A1 | 9/2003 | Phillips |
| 2003/0171809 A1 | 9/2003 | Phillips |
| 2003/0187505 A1 | 10/2003 | Liao |
| 2003/0199977 A1 | 10/2003 | Cumming |
| 2003/0204257 A1 | 10/2003 | Southard |
| 2004/0002757 A1 | 1/2004 | Lai et al. |
| 2004/0015236 A1 | 1/2004 | Sarfarazi |
| 2004/0082993 A1 | 4/2004 | Woods |
| 2004/0082994 A1 | 4/2004 | Woods et al. |
| 2004/0111152 A1 | 6/2004 | Kelman |
| 2004/0148023 A1 | 7/2004 | Shu |
| 2004/0215207 A1 | 10/2004 | Cumming |
| 2004/0220666 A1 | 11/2004 | Cumming |
| 2004/0243232 A1 | 12/2004 | Cumming |
| 2004/0249456 A1 | 12/2004 | Cumming |
| 2005/0021140 A1 | 1/2005 | Liao |
| 2005/0027354 A1 | 2/2005 | Brady et al. |
| 2005/0075732 A1 | 4/2005 | Israel |
| 2005/0096741 A1 | 5/2005 | Cumming |
| 2005/0107875 A1 | 5/2005 | Cumming |
| 2005/0125058 A1 | 6/2005 | Cumming et al. |
| 2005/0137703 A1 | 6/2005 | Chen |
| 2005/0267576 A1 | 12/2005 | Cumming |
| 2005/0288784 A1 | 12/2005 | Peyman |
| 2006/0064077 A1 | 3/2006 | Peyman |
| 2006/0064162 A1 | 3/2006 | Klima |
| 2006/0100704 A1 | 5/2006 | Blake et al. |
| 2006/0111776 A1 | 5/2006 | Glick et al. |
| 2006/0116764 A1 | 6/2006 | Simpson |
| 2006/0149369 A1 | 7/2006 | Cumming et al. |
| 2007/0032867 A1 | 2/2007 | Cumming |
| 2007/0129800 A1 | 6/2007 | Cumming |
| 2007/0129803 A1 | 6/2007 | Cumming et al. |
| 2007/0135915 A1 | 6/2007 | Klima |
| 2007/0142908 A1 | 6/2007 | Xu |
| 2007/0198084 A1 | 8/2007 | Cumming et al. |
| 2008/0027538 A1 | 1/2008 | Cumming |
| 2008/0027539 A1 | 1/2008 | Cumming |
| 2008/0027540 A1 | 1/2008 | Cumming |
| 2008/0046077 A1 | 2/2008 | Cumming |
| 2008/0086208 A1 | 4/2008 | Nordan |
| 2008/0154362 A1 | 6/2008 | Cumming |
| 2008/0281415 A1 | 11/2008 | Cumming |
| 2008/0281416 A1 | 11/2008 | Cumming |
| 2008/0288066 A1 | 11/2008 | Cumming |
| 2008/0294254 A1 | 11/2008 | Cumming et al. |
| 2008/0319545 A1 | 12/2008 | Cumming |
| 2009/0005866 A1 | 1/2009 | Cumming |
| 2009/0234449 A1 | 9/2009 | De Juan, Jr. et al. |
| 2009/0248154 A1 | 10/2009 | Dell |
| 2010/0004742 A1 | 1/2010 | Cumming |
| 2010/0057202 A1 | 3/2010 | Bogaert |
| 2011/0313519 A1 | 12/2011 | Cumming |
| 2011/0313524 A1 | 12/2011 | Cumming |
| 2011/0313525 A1 | 12/2011 | Cumming |
| 2012/0296424 A1 | 11/2012 | Betser |
| 2013/0073039 A1 | 3/2013 | Mirlay |
| 2013/0231742 A1 | 9/2013 | Deacon et al. |
| 2014/0088699 A1 | 3/2014 | Cumming |
| 2014/0094909 A1 | 4/2014 | Cumming |
| 2014/0155871 A1 | 6/2014 | Cumming |
| 2014/0172093 A1 | 6/2014 | Cumming |
| 2015/0012088 A1 | 1/2015 | Cumming |
| 2015/0073550 A1 | 3/2015 | Cumming |
| 2015/0088254 A1 | 3/2015 | Cumming |

FOREIGN PATENT DOCUMENTS

| | | |
|---|---|---|
| DE | 3626869 | 2/1988 |
| DE | 10156463 | * 11/2001 |
| FR | 2728458 | 6/1996 |
| FR | 2728459 | 6/1996 |
| FR | 2734472 | 11/1996 |
| FR | 2765797 | 1/1999 |
| FR | 2991572 | 12/2013 |
| GB | 2171912 | 9/1986 |
| GB | 2226246 | 6/1990 |
| JP | 2003-190193 | 7/2003 |
| SU | 1123685 | 11/1984 |
| WO | WO 93/05733 | 4/1993 |
| WO | WO 01/19288 | 3/2001 |
| WO | WO 01/19289 | 3/2001 |
| WO | WO 03/017873 | 3/2003 |
| WO | WO 2007/037180 | 4/2007 |
| WO | WO 2009/048656 | 4/2009 |
| WO | WO 2009/086511 | 7/2009 |

OTHER PUBLICATIONS

International Search Report and Written Opinion for PCT/US13/61452 dated Feb. 24, 2014 in 11 pages.
International Search Report and Written Opinion for PCT/US2014/057037 dated Jan. 20, 2015 in 12 pages.

* cited by examiner

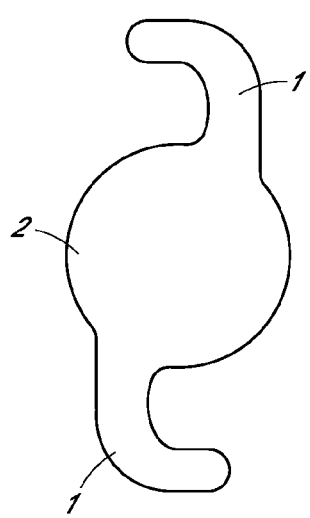
FIG. 1
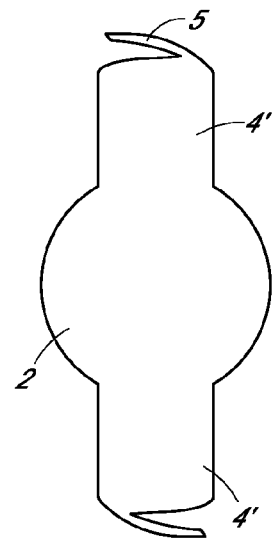
FIG. 2
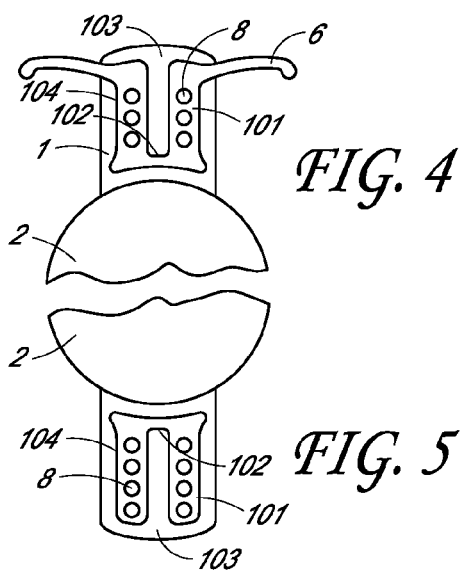
FIG. 4
FIG. 5
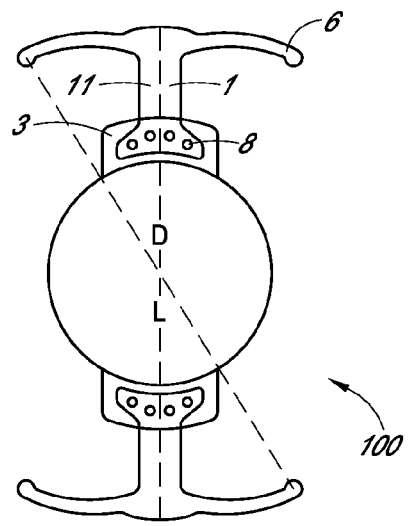
FIG. 3

ANTERIOR OPTIC VAULT

UNIPLANAR

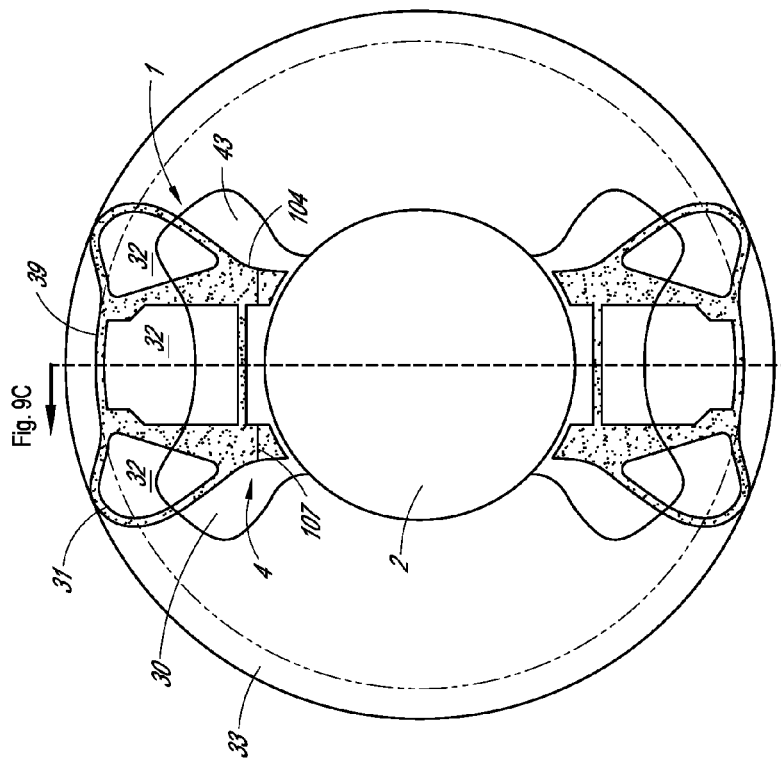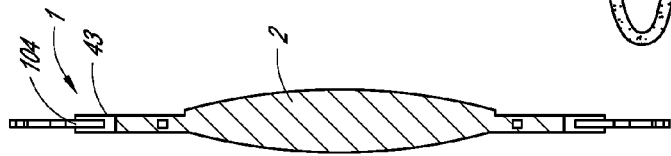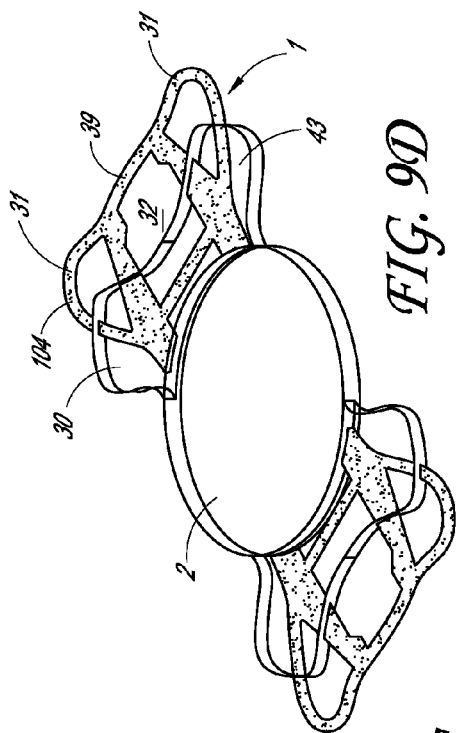

INTRAOCULAR LENS

CROSS-REFERENCE TO RELATED APPLICATIONS

This application is continuation of U.S. patent application Ser. No. 14/584,188, filed on Dec. 29, 2014, currently pending, which is a continuation-in-part of U.S. patent application Ser. No. 14/257,933, filed Apr. 21, 2014, currently pending, which is a continuation-in-part of U.S. patent application Ser. No. 14/143,612, filed Dec. 30, 2013, currently pending, and also claims priority to U.S. Provisional Application No. 61/921,782, filed Dec. 30, 2013, the contents of which are hereby incorporated by reference herein in their entireties.

BACKGROUND

Field

The present disclosure relates to intraocular lenses for implantation into the eye.

Description of the Related Art

Surgical procedures for treating cataracts that are commonly employed today involve implanting an intraocular lens (IOL) into the eye. In such procedures, a normal human lens that has been clouded over by a cataract is typically replacing by the IOL.

Many breakthrough changes in cataract surgery during the last forty years have yielded a reliable surgical procedure that regularly produces favorable patient outcomes. Modern surgical techniques also have made the operation very safe when performed by a competent surgeon.

The procedure can now also be considered a surgical means of treating myopia, hyperopia or astigmatism, as IOLs with the appropriate power to provide optical correction can be inserted in the eye.

One of the remaining problems to be solved though is to make the post-operative uncorrected distant visions (e.g., without eyeglasses or contacts) more accurate than they now are. This would then make lens surgery comparable to corneal surgery so far as the uncorrected vision is concerned, making common surgical cataract surgery or removal of a clear lens, a refractive procedure.

SUMMARY OF THE INVENTION

Recently lenses have been developed to treat presbyopia. There are two types: multifocal and accommodating. Since the light entering the eye has more than one focal point, patients implanted with multifocal lenses have problems with halos, glare, foggy vision and reduced contrast sensitivity, as less than half of the light is in focus at one time. Many of these lenses have had to be explanted because of these problems. Accommodating lenses have also been invented which were designed to move forward upon constriction of the ciliary muscle with near vision. The near vision with these lenses is not as good as that with the multifocal lenses, however they do not have the problems that are associated with multifocal lenses.

Two of the remaining problems to be solved are to make the post-operative uncorrected distance visions more accurate than they are now, and to provide excellent uncorrected distance, near and intermediate vision with a single focus lens. This would then make lens surgery comparable to corneal surgery so far as the uncorrected visions are concerned, making common surgical cataract surgery or removal of a clear lens, a refractive procedure safer and with less complications than corneal refractive and corneal presbyopic surgery.

Various embodiments described here comprise intraocular lens structures that more accurately places the optic of an intraocular lens in a more consistently repeatable and predictable location along the optical or visual axis of the eye in comparison to other lens designs, thereby making post-operative uncorrected vision (e.g., without the aid of eyeglasses or contacts) more predictable.

This disclosure, for example, describes an intraocular lens comprising rigid haptics connected to a foldable optic. Connecting the foldable optic appropriately to rigid haptics can prevent deformation of the haptics when subjected to the action of the ciliary muscle after implantation into the empty capsular bag during cataract surgery. In various embodiments described herein, two rigid haptics of substantially equal length are designed to generally leave the lens optic in the same position along the optical or visual axis of the eye as it was when it was placed into the capsular bag at the time of surgery. The lens may be designed to be slightly longer than the capsular bag or shorter, and may be uniplanar, curved or angulated, the haptic having in some embodiments a fixed angle with respect to the optic at the time of manufacture of between 5 to 40 degrees that will vault the lens optic forward or backwards upon insertion into the capsular bag.

Accordingly, various embodiments are directed toward a non-accommodating intraocular lens having at least one rigid haptic connected to a flexible optic. The rigid structure is rigid longitudinally and flexible transversely. A longitudinal length of the intraocular lens is fixed prior to insertion into the eye. The at least one haptic can be directly connected to the optic as a lens manufactured as a single piece, or indirectly connected to the optic by a short extension of the optic.

In any of the embodiments of non-accommodating lenses described herein, the force of the ciliary muscle may be insufficient of cause the optic to move, for example, anteriorly. For example, various embodiments do not have any flexible connections between the haptic and the optic (e.g., hinges, torsion bars, etc.) that allow the optic to move with respect to the haptic with movement of the ciliary muscle.

The longitudinally rigid haptic can comprise the same material as the flexible optic and be manufactured as one piece, the haptic made rigid by increasing its thickness and or its width. The rigid haptic may be made rigid by having a rigid structure; a chassis (or frame), partially or completely embedded into the flexible material of the optic such as silicone or acrylic. The rigid material of the chassis is designed to make the haptic rigid and to fixate the lens within the capsular bag of the eye. Fixation can be done using flexible loops (open or closed loops) contiguous with the internal chassis extending tangentially from the distal lateral aspects of the chassis, and/or by creating open spaces within the confines of the diameter of the optic, or by closed loops extending beyond the diameter of the optic. The loops may be made rigid or compressible. For example, these loops may be configured to remain a fixed length despite constriction of the ciliary muscle and/or fibrosis.

In any of the intraocular lens aspects described herein including those referred to above, the rigid structure can include at least one longitudinally extending strut. In certain aspects, the rigid structure can include a closed structure at least partially surrounding the at least one longitudinally extending strut to form at least one open area (e.g., one, two, or three open areas). In certain aspects, the loop structure can include a first width and a second width. The first width can be closer to a distal end of the loop structure, and the first width can be greater than the second width. In certain aspects, the loop structure can have a width that is less than the width of the at least one longitudinally extending strut. For example, the width of the loop structure can be less than about 25% and/or greater than about 5% of the widths of the at least one longitudinally extending strut (e.g., less than 20%, less than 15%, or less than 10%).

In any of the intraocular lens aspects described herein including those referred to above, the rigid haptics may have T shaped flexible fingers at the distal end of the otherwise rigid haptic.

In any of the intraocular lens aspects described herein including those referred to above, the rigid structure can be a plate haptic. The plate haptic can include a thin bar disposed at either the distal or proximal end of the haptic. Further, the plate haptic can include an open area proximal to the thin bar.

In any of the intraocular lens aspects herein including those referred to above, the optic can be uniplanar or biased posteriorly or anteriorly at the time of manufacture, prior to insertion into an eye. The structures also can have a fixed length that can resist deformation by the action of the ciliary muscle.

Accordingly, various embodiments disclosed herein may comprise an intraocular lens comprising flexible optic and at least one haptic connected to the optic. The at least one haptic comprises a rigid structure. The intraocular lens comprises a non-accommodating IOL having a longitudinal length that is fixed.

Various embodiments comprise an intraocular lens comprising a flexible optic and at least one haptic connected to the optic wherein the rigid haptic is more rigid than the flexible optic. In such embodiments, the intraocular lens may comprise a non-accommodating IOL.

Various embodiments comprise an intraocular lens where the flexible optic may connect to a haptic of the same material and the haptic is made rigid by being widening or thickening its structure or by a combination of both. In some embodiments, the intraocular lens entirely comprises the same material (e.g., acrylic). In certain embodiments, the intraocular lens comprises a monolithic structure.

As discussed above, in any of the embodiments of non-accommodating lenses described herein, the force of the ciliary muscle may be insufficient of cause the optic to move, for example, anteriorly. For example, various embodiments do not have any flexible connections between the haptic and the optic (e.g., hinges, torsion bars, etc.) that allow the optic to move with respect to the haptic in response to movement of the ciliary muscle.

Certain aspects of the present disclosure relate to non-accommodating single focus intraocular lenses configured to provide uncorrected vision at all distances. The lens has haptics and an optic comprising a semi-rigid acrylic that can be deformed for implantation into the eye through a small incision, but can regain its optical and physical properties after implantation into the eye and resist deformation when force is applied by the ciliary muscle and by fibrosis.

Certain aspects of the disclosure are directed toward an intraocular lens having a single-focus, acrylic optic and at least one semi-rigid, acrylic haptic connected to the optic. The intraocular lens can have a fixed longitudinal length (e.g., the same fixed length pre-operatively and post-operatively). The intraocular lens can resist deformation, despite contraction and relaxation of the ciliary muscle and fibrosis within the capsular bag, after implantation into the eye using, for example, the semi-rigid haptics described herein. The intraocular lens can be sufficiently flexible to be compressed from an original configuration to a compressed configuration for insertion into the eye through a small incision and return to a normal shape (e.g., uncompressed shape) after implantation into the eye.

In some embodiments, the intraocular lens described above can be configured to provide uncorrected visional at near, intermediate, and far distances.

In any of the single-focus intraocular lens aspects described herein including those referred to above, the optic can be biased backwards at a fixed angle relative to the distal end of at least one haptic. The bias can remain unchanged after implantation into the eye. Moreover, in some embodiments, the vault angle can remain unchanged after implantation into the eye. In certain aspects, the at least one haptic can be biased anteriorly. In certain aspects, the at least one haptic can include two haptics that are both biased anteriorly. In certain aspects, the vault angle can be between about 1 degree and about 50 degrees.

In any of the single-focus intraocular lens aspects described herein including those referred to above, the semi-rigid haptic can include at least one longitudinally extending strut. In certain aspects, the rigid structure can include a closed structure at least partially surrounding the at least one longitudinally extending strut to form at least one open area (e.g., one, two, or three open areas). In certain aspects, the loop structure can include a first width and a second width. The first width can be closer to a distal end of the loop structure, and the first width can be greater than the second width. In certain aspects, the loop structure can have a width that is less than the width of the at least one longitudinally extending strut. For example, the width of the loop structure can be less than about 25% and/or greater than about 5% of the width of the at least one longitudinally extending strut (e.g., less than 20%, less than 15%, or less than 10%).

In any of the single-focus intraocular lens aspects described herein including those referred to above, the semi-rigid haptics may have compressible lateral flexible fingers at the distal end of the otherwise semi-rigid haptic to form a T-shaped haptic.

In any of the single-focus intraocular lens aspects described herein including those referred to above, the semi-rigid structure can be a plate haptic. The plate haptic can include flexible thin distal lateral fingers forming a T-shaped haptic.

In any of the single-focus intraocular lens aspects described herein including those referred to above, the semi-rigid haptic may be more rigid than the flexible optic. The optic can be flexible at its thin circumference and semi-rigid at its center, thus allowing it to be folded into a longitudinally elongate configuration to be inserted through a small incision into the eye having a length of less than or equal to about 3.0 mm, preferably less than or equal to about 2.5 mm.

In various embodiments, the intraocular lens can be a non-accommodating IOL. In certain embodiments, this non-accommodating IOL is designed to provide distance, intermediate and near vision. In certain embodiments, this non-accommodating IOL provides such vision without the problems of glare, halos and foggy vision and reduced contrast experienced with multifocal intra ocular lenses.

In any of the single-focus intraocular lens aspects described herein including those referred to above, the posterior vaulted optic connects to a haptic of the same semi-rigid material, the haptic made more rigid by widening or thickening its structure or by a combination of both.

Certain aspects of the disclosure are directed toward a non-accommodating intraocular lens having a single-focus optic and at least one semi-rigid haptic connected to the optic. The optic can be pre-operatively vaulted (e.g., posteriorly) at a fixed angle relative to the at least one haptic. The optic may remain vaulted after implantation, and in some embodiments, the vault angle can remain unchanged after implantation. The semi-rigid haptic can be sufficiently flexible to be compressed for insertion into the eye through a small incision and assume a normal, uncompressed shape after implantation into the eye. In some embodiments, the lens can be configured to provide uncorrected visional at near, intermediate, and far distances.

In any of the non-accommodating intraocular lenses described herein including those referred to above, the at least one semi-rigid haptic can be biased anteriorly. In certain aspects, the at least one semi-rigid haptic includes two haptics that are both biased anteriorly.

In any of the non-accommodating intraocular lenses described herein including those referred to above, the vault angle can be between about 1 degree and about 50 degrees, such as between about 5 degrees and about 40 degrees.

In any of the non-accommodating intraocular lenses described herein including those referred to above, the optic and the at least one haptic can include a same material (e.g., acrylic or silicone). Certain aspects of the disclosure are directed toward implanting a non-accommodating intraocular lens having an optic connected to at least one haptic. The intraocular lens can have any of the features described herein. Pre-operatively the intraocular lens can be vaulted at posteriorly at a fixed angle relative to the at least one haptic. The intraocular lens can be compressed for insertion into the eye through a small incision. After implantation, the intraocular lens can assume a normal, uncompressed shape that is resistant enough to withstand the pressure changes within the eye, e.g., caused by the ciliary muscle attempting to accommodate or by fibrosis. After implantation, the intraocular lens can remain vaulted and in some embodiments, may remain vaulted at the same fixed angle.

Certain aspects of the disclosure are directed toward a non-accommodating intraocular lens having a single-focus, acrylic optic and at least one haptic connected to the optic. The optic cam be pre-operatively vaulted at a fixed angle relative to the at least one haptic. The optic can remain vaulted after implantation and in some embodiments, the vault angle can remain unchanged after implantation. In some embodiments, the intraocular lens can be configured to provide uncorrected visional at near, intermediate, and far distances.

In any of the non-accommodating intraocular lenses described herein including those referred to above, the at least one haptic can be biased anteriorly. In certain aspects, the at least one haptic can include two anteriorly biased haptics.

In any of the non-accommodating intraocular lenses described herein including those referred to above, the vault angle can be between about 1 degree and 50 degrees, such as between about 5 degrees and about 40 degrees.

In any of the non-accommodating intraocular lenses described herein including those referred to above, the optic and the at least one haptic can include a same material.

Certain aspects of the disclosure are directed toward an accommodating intraocular lens comprising a lens optic and a pair of opposing plate haptics coupled to the lens optic. Each plate haptic can include a rigid frame at least partially embedded in a flexible component. The rigid frame can include a number of openings along a distal portion of the frame. At least a portion of at least some of the openings can extend beyond a distal edge of the flexible component. A transverse width of the rigid frame measured between opposing lateral edges of the rigid frame can be larger than a transverse width of the flexible component measured between opposing lateral edges of the flexible component. The rigid frame can extend beyond a proximal edge of the flexible component.

In any of the accommodating intraocular lenses described herein including those referred to above, each plate haptic can include a connecting portion connected to the optic. The connecting portion can include a short appendage connected to the optic and at least one connecting bar extending laterally from the short appendage. The at least one connecting bar can include a first connecting bar and a second connecting bar. The first and second connecting bars can extend laterally from opposing lateral sides of the short appendage.

In any of the accommodating intraocular lenses describe herein including those referred to above, each plate haptic can include an elongate slot.

In any of the accommodating intraocular lenses described herein including those referred to above, each plate haptic can include at least one anterior protrusion extending anteriorly from said plate haptic.

In any of the accommodating intraocular lenses described herein including those referred to above, each plate haptic can include opposing lateral paddles. A transverse width measured between outer lateral edges of opposing paddles of the same haptic can be greater than a transverse width of the optic.

Certain aspects of the disclosure are directed toward an accommodating intraocular lens comprising a lens optic and a pair of opposing plate haptics coupled to the lens optic. Each plate haptic can include a rigid frame having a number of openings.

In any of the accommodating intraocular lenses described herein including those referred to above the rigid frame is at least partially embedded in a flexible component. In some embodiments the rigid frame can includes a number of openings along a distal portion of the frame. In various embodiments, some of the at least a portion of at least some of the openings can extend beyond a distal edge of the flexible component. In some embodiments, the rigid frame extends beyond a proximal edge of the flexible component.

In any of the accommodating intraocular lenses described herein including those referred to above, a transverse width of the rigid frame measured between opposing lateral edges of the rigid frame is larger than a transverse width of the flexible component measured between opposing lateral edges of the flexible component.

In any of the accommodating intraocular lenses described herein including those referred to above, each plate haptic can include a connecting portion connected to the optic. The connecting portion can include a short appendage connected to the optic and at least one connecting bar extending laterally from the short appendage. The at least one connecting bar can include a first connecting bar and a second connecting bar. The first and second connecting bars can extend laterally from opposing lateral sides of the short appendage.

In any of the accommodating intraocular lenses describe herein including those referred to above, each plate haptic can include an elongate slot.

In any of the accommodating intraocular lenses described herein including those referred to above, each plate haptic can include at least one anterior protrusion extending anteriorly from said plate haptic.

Any of the intraocular lenses described herein including those referred to above, can include first and second plate haptics, wherein the first plate haptic is coupled to the optic at a set first non-zero angle between the optic and the first plate haptic, and wherein the second haptic is coupled to the optic at a set second non-zero angle between the optic and the second plate haptic, the second non-zero angle being different from the first non-zero angle. In various embodiments, the lens is configured such that, when the lens is placed into a capsular bag of an eye, a superior hemisphere of the optic is positioned at a 12 o'clock position and posterior to an inferior hemisphere. In some embodiments the superior hemisphere is configured to focus light for distant vision. In certain embodiments, the first non-zero angle is not less than 10 degrees and not more than 50 degrees. Also, in certain embodiments, the second non-zero angle is at least about 20 degrees and less than or equal to about 50 degrees.

Also, in any of the intraocular lenses described herein including those referred to above, the optic may be a progressive powered lens including a gradient of increasing power, e.g., providing for far vision in a superior hemisphere of the optic and providing for near vision in an inferior hemisphere of the optic when implanted in the eye.

A wide variety of variations are possible. For example, any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 1 illustrates a non-accommodating lens with loops (e.g. open loops) that comprises an optic that can be posteriorly vaulted and haptics in one piece comprising one material, for example acrylic. The haptics can be wider than traditional loop haptics and be manufactured flat.

FIG. 2 illustrates a plate haptic non-accommodating intraocular lens (NAIL) with small fixation loops all made of one piece. The optic can be posteriorly vaulted.

FIG. 3 illustrates an embodiment of a haptic having a single rigid longitudinal structure with T shaped flexible distal lateral extensions.

FIG. 4 illustrates a non-accommodating intraocular lens (NAIL) having a chassis embedded into the same flexible material as the optic.

FIG. 5 is the same as FIG. 4 but without the fixation loops.

FIGS. 9A-9D illustrate a rigid haptic intraocular lens having a triple loop structure, the three loops (e.g. closed loops) being partially covered with the same flexible material as the optic.

DETAILED DESCRIPTION OF THE PREFERRED EMBODIMENTS

Figure 6:
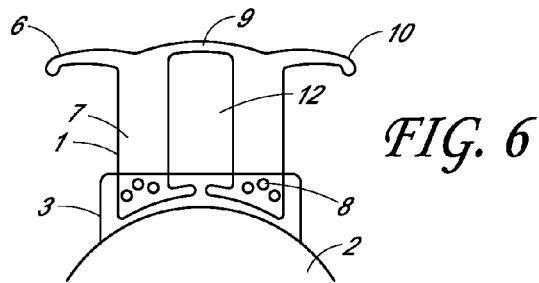
FIG. 6 illustrates another NAIL having two exposed rigid longitudinal plates or struts connected by a thin transverse bar creating an enclosed open space and fixation loops (e.g. open loops) to facilitate fixation of the lens into the capsular bag. The lens may be designed without the flexible fingers since fixation can occur over the transverse thin bar 9. The thin arm 9 can have a width that is less than a width of the longitudinal plate or struts 7.

Many intraocular lenses have an optic connected to two or more flexible haptics, which function to center and fixate the lens in the empty capsular bag of the human lens. These haptics can be formed by two flexible loops.

The circular ciliary muscle inside the eye, part of the autonomic nervous system and active throughout life, is responsible for changing the focus of the eye. When the patient implanted with standard loop intraocular lenses attempts to see during the early post-operative period subsequent to cataract surgery, the ciliary muscle, still active, applies end-to-end pressure (e.g., in the longitudinal direction of the lens) that impinges on the flexible loops moving them forwards and backwards, centrally and peripherally within the capsular bag. This movement can shift the location of the lens in the capsular bag. Also during this time, fibrosis is taking place and the loops do not necessarily end up fixed in the cul-de-sac of the bag where they were placed at the time of surgery. Instead, the loops may be, for example, stuck somewhere between the cul-de-sac of the capsular bag and the optic. Changing the location of the haptic loops within the bag can also change the position of the lens optic along the axis of the eye and cause decentration and tilting of the optic. In some flexible loop designs, the flimsy flexible loops at the time of manufacture are significantly longer than the 10 mm diameter of the capsular bag (e.g., up to 12 mm long) and may impinge through the capsular bag wall to impinge on the ciliary muscle. The haptics can be flimsy and easily deformed by the pressures exerted on them during the early post-operative period. The lens position is thus not where it was calculated and anticipated to be. Consequently, the uncorrected distance vision (e.g. without glasses or contact lenses) and post-operative refractions are not what was expected prior to surgery. In some cases, the loops of a lens have been compressed centrally to lie in front or behind, the lens optic.

Various embodiments described here comprise intraocular lens structures that more accurately place the optic of an intraocular lens in a more consistently repeatable and predictable location along the optical or visual axis of the eye in comparison to other lens designs, thereby making post-operative uncorrectable vision (e.g., without the aid of eyeglasses or contacts) more predictable.

Non-Accommodating Lenses

See, for example, the intraocular implants illustrated in FIGS. 1-4. The intraocular implants comprise an optic 2 and opposing rigid haptics 1 (e.g., plate haptics) and optionally with flexible loop lateral extensions 6 (e.g. open loops) (see FIGS. 3 and 4). In FIGS. 4 through 8 only one of the two haptics, however, is shown in these figures. The haptics 1 can be connected to the optic 2 either directly (see FIGS. 1 and 2) or to a short thick rigid extension 3 of the optic 2 (see FIGS. 3 to 8), and either constructed as a single piece (e.g., monolithic) at the time of manufacture or separately formed and connected together. The short extension 3 can be constructed from the same material as the optic 2. Further, the short rigid extension 3 can be integrally molded with the optic 2 or separately formed from the optic 2. To facilitate connection, holes 8 are made through the rigid component of the haptic through which the flexible component 103 or rigid extension 3 can fuse during the manufacturing process (see FIGS. 3-8). The short thick rigid extension 3 may be desirable to facilitate the connection between the optic 2 and the haptic 1 without encroaching on the circumference of the optic 2.

The optic 2 may comprise substantially transparent biocompatible flexible optical material, e.g. acrylic, hydrogel, or silicone, and may be biconvex, plano convex, concave/plano, toric, aspheric, spherical Fresnel multifocal or any combination. The optic 2 may be a progressive powered lens including a gradient of increasing power, e.g., providing for far vision in a superior hemisphere of the optic and providing for near vision in an inferior hemisphere of the optic when implanted in the eye. The optic 2 may be used in combination with a second optic within the eye.

The haptics 1 can be designed to be rigid and resistant to deformation from the action of the ciliary muscle. In particular, the haptics may resist pressure imposed in the longitudinal direction by the ciliary muscle without flexing. Unlike flexible haptics that are traditionally used with non-accommodating and accommodating lenses, the rigid haptics 1 better facilitate centration and provide a more consistent location of the optic along the axis of the eye because the rigid haptics 1 are resistant to compression.

As illustrated in FIG. 1, in some embodiments, the haptics 1 can include an open loop. Some haptics 1 can include one or more closed loops. (See also FIGS. 6 to 9 discussed more fully below).

FIG. 1 shows a lens manufactured for example from acrylic as one piece, with the optic 2 contiguous with the curved open loop like rigid haptic 1. As with all these lens designs the lens may be uniplanar or the optic 2 may be vaulted backwards or forwards at the time of surgery.

FIG. 2 shows a lens manufactured of one material (e.g., acrylic) with a rigid plate-like haptic structure 4' and small distal fixation fingers 5.

FIG. 3 schematically illustrates an embodiment of a haptic 1 having a single rigid longitudinal structure 11 and forming a T-shape with flexible distal lateral extensions 6, the rigid longitudinal structure 11 attached to a short thickened extension 3 of the optic 2 or connected to the optic 2.

FIGS. 4 and 5 show a haptic 1 including a chassis 104 including two rigid struts/plates 101 and a proximal transverse connecting bar 102 between the two struts/plates 101 (at the proximal end thereof). The chassis 104 which is embedded into the flexible optical material 103 has external distal fixation fingers 6 in FIG. 4.

FIG. 6 illustrates a haptic 1 including two rigid struts/plates 7, with finger like extensions 6, with knob like peripheral ends 10, embedded proximally into a thick rigid extension 3 of the optic 2 or connected to the optic, anchored to it by fusion of the flexible material through holes 8, during the manufacturing process. The two plates 7 connected distally by a thin transverse crossbar 9. The two rigid struts/plate 7 and the transverse crossbar 9 form an open space longitudinally between the transverse crossbar 9 and the optic 2.

Figure 7:
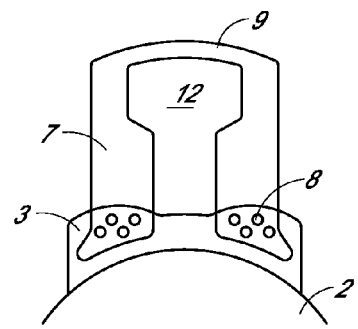
FIG. 7 illustrates yet another NAIL having longitudinal plates or struts connected by a thin transverse bar, but without the fixation loops.

FIG. 7 is similar to FIG. 6 except that fixation into the capsular bag is achieved without the flexible fingers 6 by fusion of the anterior and posterior capsules over the distal thin connecting bar 9 to fibrose through the open space 12 enclosed by the struts/plates 7, bar 9 and thick rigid extension 3. The width of each strut could be between 1.0 and 3.0 mm so that the lens can be folded longitudinally to be compressed to be inserted through an incision of 3.0 mm or less.

Figure 8:
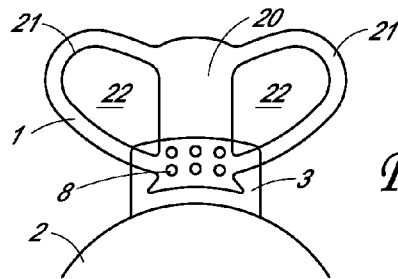
FIG. 8 illustrates another embodiment of a haptic having a rigid haptic double loop structure.

FIG. 8 illustrates a haptic 1 comprising a single plate 20 to which is attached on each of its lateral sides two rigid closed loops 21 to provide two enclosed spaces 22 or openings into which the capsular bag can fibrose to fix the lens haptics 1 within the capsular bag.

Figure 10:
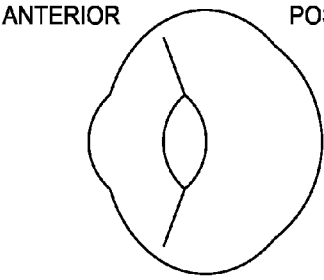
FIG. 10 illustrates a side view of an intraocular lens optic with the optic vaulted posteriorly.
Figure 11:
FIG. 11 illustrates a side view of an intraocular lens optic vaulted anteriorly.
Figure 12:
FIG. 12 illustrates a side view of an intraocular lens having haptics disposed in a common plane.

FIGS. 10, 11, and 12 show the possible side elevations of the lens, which can be vaulted posteriorly (FIG. 10), anteriorly (FIG. 11) and uniplanar (FIG. 12). FIGS. 10 and 11 show the optic vaulted posteriorly and anteriorly, respectively, with respect to the distal end of the haptic when implanted. This lens shown in FIG. 10, for example, may comprise a uniplanar accommodating lens such as described herein that is vaulted upon implantation. As discussed herein, this lens shown in FIG. 10 may also be manufactured so as to bias the haptic (e.g., anteriorly) with respect to the optic to increase the depth of focus. When the optic is vaulted posteriorly with respect to the distal end of the haptic, the optic may potentially be at a position suitable to increase depth of focus.

Figure 12A:
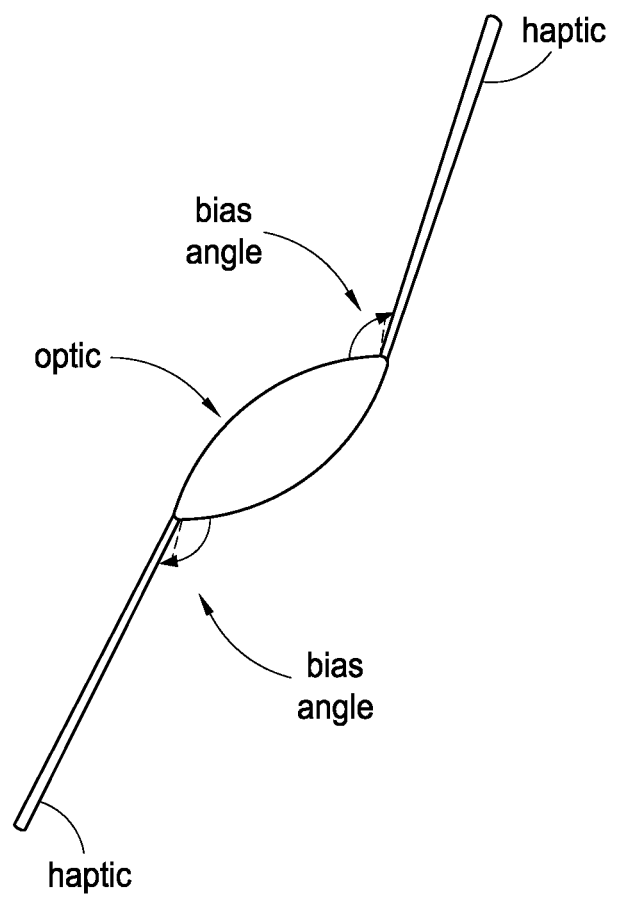
FIG. 12A is a schematic illustration showing a lens comprising an optic and haptics configured in a stretched "z" shape.
Figure 12B:
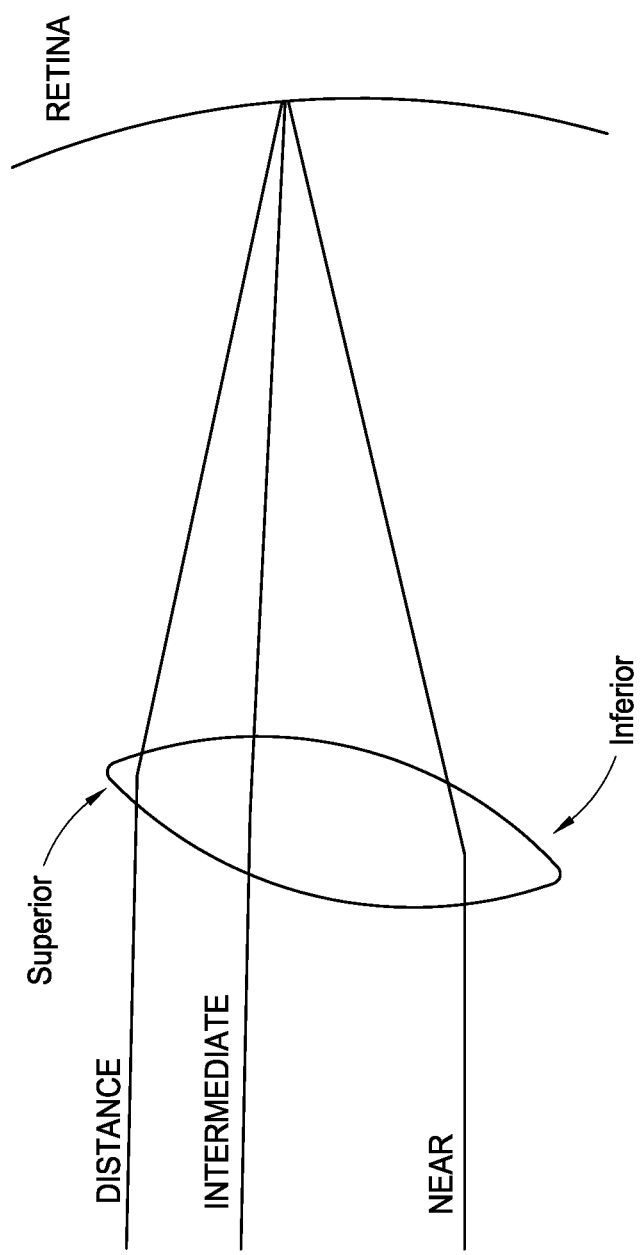
FIG. 12B is a schematic illustration showing how tilting the optic can result in focusing for far, near, and intermediate distances on the retina.

In other embodiments, such as shown in FIG. 12A, each of the haptics can be biased or fixed in a different direction, such that the lens forms a stretched out z-shape, e.g., a first haptic can be biased or fixed in an anterior direction and a second haptic can be biased or fixed in a posterior direction, for example with respect to the optic. Each of the haptics can be biased or fixed at a non-zero angle relative to the optic. The first haptic can be biased or fixed at a first non-zero angle, and the second haptic can be biased or fixed at a second non-zero angle different from the first non-zero angle. With the haptics biased in different directions, the optic can be tilted, as shown in FIG. 12B, such that the superior hemisphere of the optic is posteriorly biased and the inferior hemisphere of the optic is anteriorly biased when the lens is placed into a capsular bag. In this configuration, the superior hemisphere can be positioned to improve distance vision, while the inferior hemisphere can be positioned to improve near vision when implanted in the eye. Such biasing is discussed in U.S. patent application Ser. No. 13/953,605 published as U.S. Patent Publication No. 2014/0172093, filed on Jul. 29, 2013, which is incorporated herein by reference in its entirety.

Figure 13:
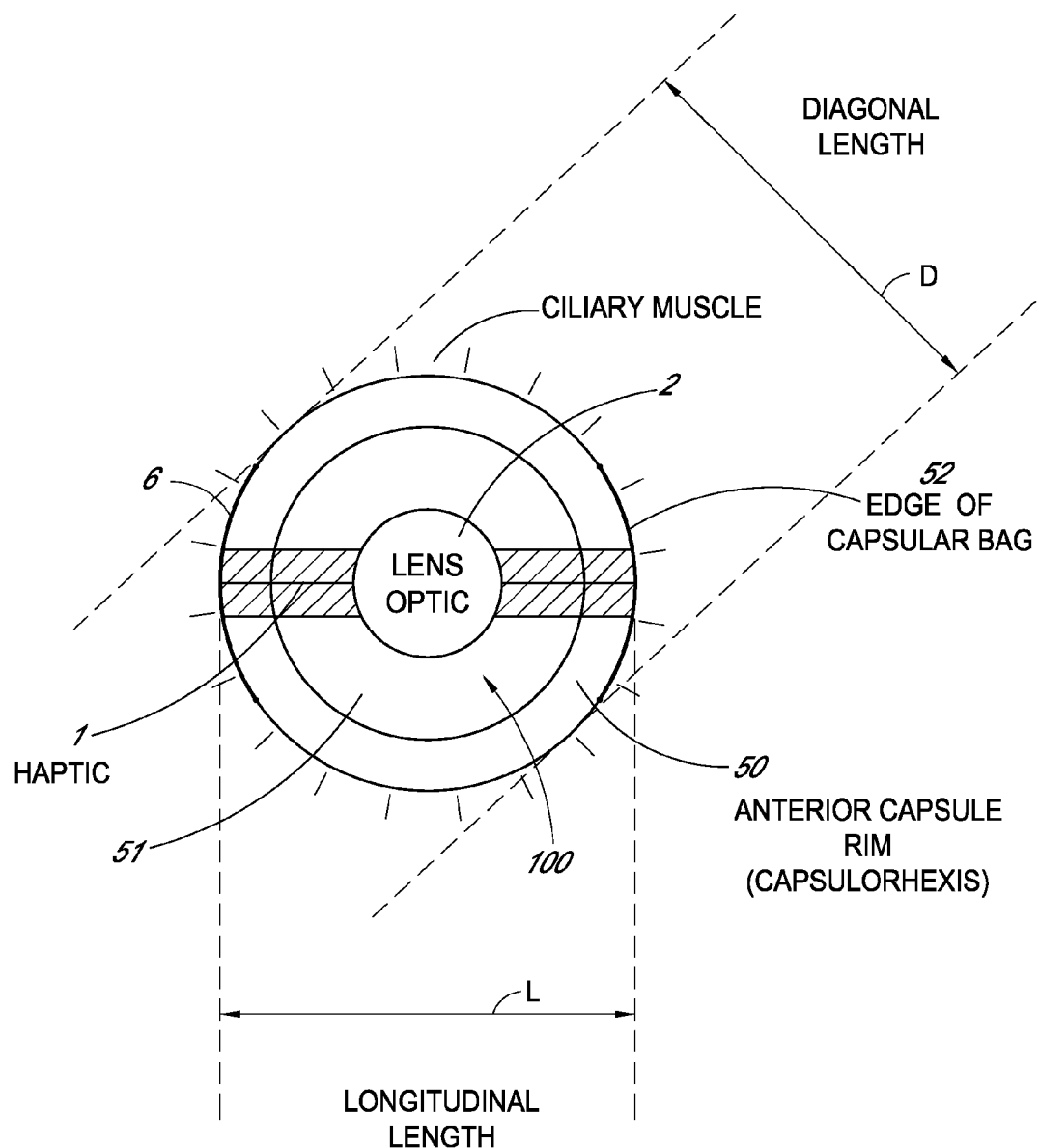
FIG. 13 illustrates a schematic diagram of an intraocular lens implanted in a capsular bag.

FIG. 13 shows a schematic of the non-accommodating intraocular lens 100 within the capsular bag. Visible are the anterior capsule rim 50, the posterior capsule 51 and the edge of the capsular bag 52 inside of which is the bag cul-de-sac.

The lenses described above are designed to have a flexible optic 2 connected to rigid haptics 1 (e.g., plate haptics) that are rigid longitudinally so that the lens can be compressed into an insertion device to be inserted into the eye through an incision of 3.0 mm or less. The haptics 1 are rigid enough to prevent flexion in the longitudinal direction when subjected to the pressure exerted on them by action of the ciliary muscle and fibrosis. The thin transverse connecting bars 9 of the chassis 104, when present, are flexible to enable the lenses to be folded and compressed about the longitudinal axis.

In various embodiments, the overall length D of the lens 100 may be from about 9.5 mm to about 14.0 mm as measured diagonally from the tips of the fixation lateral loops 6 on opposite sides of the lens 100. See, e.g., FIGS. 3 and 13. The diagonal distance D extends through the center of the optic 2. The longitudinal length L of the lens 100 (also shown in FIGS. 3 and 13) can be at least the diameter of the average capsular bag. For example, the longitudinal length of the lens 100 can be from about 9.5 mm to about 12.0 mm, the preferred length being about 10.5 mm in various embodiments, which is slightly longer than the average capsular bag diameter, in certain embodiments. When the length of the lens 100 is less than or equal to about 10.5 mm, the lens 100 does not deform the capsular bag and does not impinge on the ciliary muscle.

The haptic component 3 extending from the flexible optic 2 is made rigid in some embodiments by its small length, less than 1 mm, and a thickness more than 1 mm and may comprise at least in part acrylic, silicone or other inert flexible material, and the rigid component, polyimide, acrylic or other rigid materials. The haptic 1 may be made rigid longitudinally, provided in some embodiments by the combination of a rigid material 104 embedded within a flexible material 103. The rigid struts and/or plates 7 may comprise polyimide, prolene or any derivative of nylon, PMMA titanium or other rigid or inert material, or a combination of rigid and flexible materials to make the haptics 1 rigid longitudinally.

In some embodiments, the intraocular lens can include at least one semi-rigid haptic (e.g., two, three, or more) and an optic. In some embodiments, the at least one semi-rigid haptic and the optic can comprise a same material (e.g., acrylic). In some embodiments, the intraocular lens can be monolithic or a single piece. The semi-rigid haptics and optic may be foldable, in order to insert the optic through a small incision into the eye. However, after insertion and regaining its shape it is resistant enough to withstand the pressure changes within the eye that occur with contraction and relaxation of the ciliary muscle and from the forces that occur during postoperative fibrosis. The two semi-rigid haptics can have equal length. Resistance to deformation by the action of the ciliary muscle and fibrosis leave the lens optic in substantially the same position along the optical or visual axis of the eye as it was when it was placed into the empty capsular bag at the time of surgery. The lens may be designed to be slightly longer, or shorter, than the capsular bag and the haptic (e.g., the distal end of the haptic) may be angulated with respect to the optic, having a fixed angle at the time of manufacture, of between about 1 degree and 50 degrees, such as between about 5 degrees and about 40 degrees (e.g., between about 5 degrees and about 20 degrees, between about 10 degrees and about 25 degrees, or between about 15 and about 40 degrees), to, for example, achieve optimal depth of focus. This will position the lens optic in a posterior position relative to the distal ends of the haptics upon insertion into the capsular bag.

Various embodiments are directed toward a non-accommodating intraocular lens with the optic manufactured in one piece with the optic biased or vaulted backwards with respect to the distal end of the haptic, wherein the bias or vault angle may be the same on both optic/haptics junctions. The semi-rigid lens structure can be resistant to deformation by the ciliary muscle and fibrosis, but can be foldable longitudinally to be inserted through an incision of less than 4.0 mm into the capsular bag of the eye.

The overall longitudinal length of the lens can be between about 9.5 and about 12 mm, which may be slightly longer than the capsular bag, preferably about 10.5 mm. When the length of the lens 100 is less than or equal to about 10.5 mm, the lens 100 does not deform the capsular bag and does not impinge on the ciliary muscle.

Both semi-rigid haptics can be the same length. The diameter of the optic can be between 4.0 and 8 mm with a thin center thickness between about 0.2 and about 2.0 mm. Since the semi-rigid material is resistant to deformation by the ciliary muscle and fibrosis, the haptics cannot be significantly deformed and, therefore, the lens optic is in the same position post operatively as it was at the time of surgery. Similarly, orientation of the intraocular lens can be the same post-operatively as pre-operatively both along the axis of the eye and on a rotational axis should a toric lens be implanted. This makes the predictability of the post-operative effective lens position (ELP) along the visual axis of the eye more accurate and, therefore, the uncorrected visions are more predictable. The longitudinal length of the intraocular lens can be fixed prior to insertion into the eye, e.g., the longitudinal length of the intraocular lens can be the same pre-operatively and post-operatively. However, the lens may have thin flexible distal lateral fingers resulting in the transverse diameter being longer than the longitudinal diameter. These flexible fingers can be designed to fixate the lens within the capsular bag and prevent rotation of the lens when a toric optic is part of the lens design.

As discussed above, the longitudinally rigid haptic can comprise the same material as the flexible optic and be manufactured as one piece. The semi-rigid haptic can be made more rigid by increasing its thickness and/or its width. Fixation can be done using flexible loops (open or closed loops) contiguous with the lens body extending tangentially from the distal lateral aspects of the plate haptic design, or by creating open spaces within the confines of the diameter of the haptic, and/or by closed loops extending beyond the diameter of the optic. The loops of the semi-rigid material may be thin to be flexible and compressible, but rigid enough to maintain the length of the lens when subject to forces from the ciliary muscle.

Figure 15:
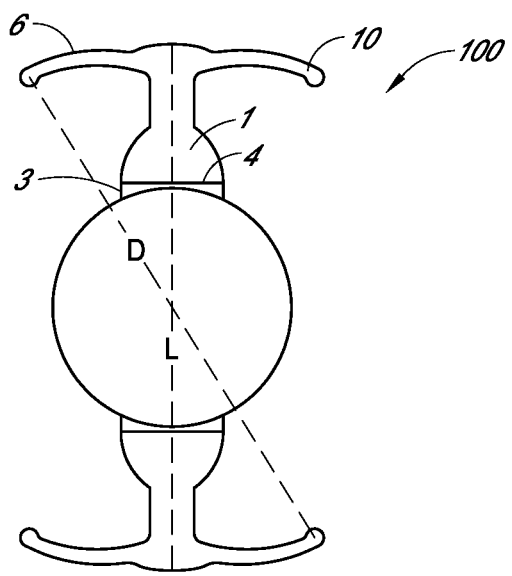
FIG. 15 illustrates an embodiment of a haptic having a single thick rigid longitudinal anteriorly biased or vaulted haptic structure with T-shaped flexible distal lateral extensions.
Figure 16:
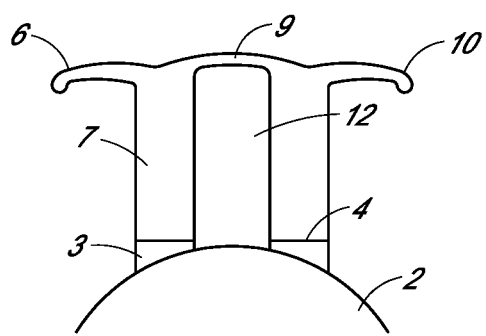
FIG. 16 illustrates another lens design having two thick rigid longitudinal plates or struts 7 connected by a thin, transverse bar 9 creating an enclosed open space 12 (e.g. closed loops) to facilitate fixation of the lens into the capsular bag along with distal lateral thin flexible fingers 6. The lens may be designed without the flexible fingers since fixation can occur over the transverse thin bar 9. The thin arm 9 can have a width that is less than a width of the longitudinal plate or struts 7.
Figure 17:
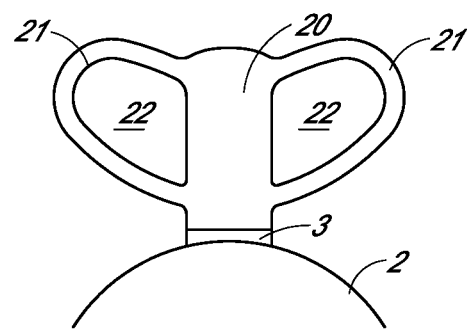
FIG. 17 is a lens design with a thick central longitudinal plate 20 having a width of less than about 3.0 mm and two closed loops 21 providing two open spaces 22 for fixation of the lens into the capsular bag.

Various embodiments disclosed herein, however, can address the problems discussed above. See, for example, the intraocular implants illustrated in FIG. 15. The intraocular implants comprise an optic 2 and opposing anteriorly biased semi-rigid haptics 1, directly connected to the optic at the flexed junction 4, with flexible loop lateral extensions 6 (e.g. open loops). In FIGS. 16-18, only one of the two halves of the lens is shown. The lens can have two-fold symmetry, such that the other half is the same as that shown. A short optic extension 3 can include the rigidly flexed junction 4 between the optic 2 and the haptic 1. The optic 2 and haptics 1 can be constructed from the same material (e.g., acrylic). The short optic extension 3 may be desirable to facilitate the connection between the optic 2 and the haptic 1 without the haptic 1 encroaching on the circumference of the optic 2. The intraocular lenses in FIGS. 16-18 can include any of the features described in connection with FIGS. 3, 6, 8; however, unlike those figures, the haptic 1 does not include through holes through which the optic extension 3 can extend although these embodiments could also include through holes. Likewise, the any of the features or combinations of features of the embodiments shown in any of FIGS. 15-18 can be included in any of the other lenses shown in FIGS. 1-7. For example, the flexed junction 4 shown in FIGS. 15-18 (as well as FIG. 9) can be included in FIGS. 1-2.

The lens may comprise a transparent biocompatible flexible optical material, such as acrylic, and the optic may be biconvex, plano convex, concave/plano, toric, aspheric, spherical, Fresnel, multifocal or any combination, thereof. The optic 2 may be a progressive powered lens including a gradient of increasing power, e.g., providing for near vision in an inferior hemisphere of the optic and providing for distance in vision in a superior hemisphere of the optic when implanted in the eye.

The haptics 1, in at least the longitudinal direction, are designed to be semi-rigid and resistant to deformation from the action of the ciliary muscle or by fibrosis. Unlike flexible haptics that are traditionally used with non-accommodating and accommodating lenses, the semi-rigid longitudinal haptics 1 better facilitate centration and provide a more consistent location of the optic along the axis of the eye because the longitudinally semi-rigid haptics 1 are resistant to deformation caused by the ciliary muscle and fibrosis.

In embodiments of the intraocular lenses described herein, the overall length of the lens 100 may be from about 9.5 mm to about 12.0 mm, and from about 11.0 mm to about 14.0 mm as measured diagonally across the lens from the tips 10 of the fixation flexible lateral loops 6 on opposite sides of the lens. See, e.g., FIG. 15. The lateral loops 6 can include orientation members 10 (e.g., round or oval knobs, one on each end of the fixation members) at an end of the lateral loops 6. The diagonal distance extends through the center of the optic. The longitudinal length L of the lens 100 (also shown in FIG. 3) can be at least the diameter of the average capsular bag. For example, the preferred longitudinal length can be about 10.5 mm. When the length of the lens 100 is less than or equal to about 10.5 mm, the lens 100 does not deform the capsular bag and does not impinge on the ciliary muscle.

The short optic extension 3 extending from the flexible optic can be made more rigid in some embodiments by its shorter length of less than 1 mm, and its thickness.

Figure 18A:
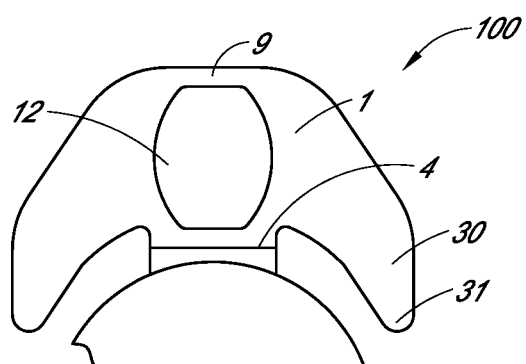
FIG. 18A illustrates one-half of a lens with a haptic 1 having lateral members (or paddles) 30. The haptic 1 can be wider than the optic 2, and the tip 31 of the lateral members 30 can be designed to lie posterior to the optic after implantation. The haptic 1 forms a closed loop 12.

As shown in FIG. 18A, the haptics 1 can have lateral members (or paddles as referred to elsewhere herein) 30 and a transverse bar 9 extending between the lateral extension members 30. The haptic 1 can be wider than the optic 2 (e.g., the lateral distance between the lateral extension members 30 on opposite sides of the optic as compared to the width or diameter of the optic), and the tip 31 of the lateral members 30 can be designed to lie posterior to the optic when implanted. The lateral members 30 can thus be increasingly curved toward the tip 31. The haptic 1 can form a closed loop 12 (and open region). The intraocular lens can include a short optic extension 3 across which is the rigidly flexed junction 4 between the optic 2 and the haptic 1. This flexed junction 4 allows for the haptics to be biased as an angle with respect to the optics at the time of manufacture as described herein. In some embodiments, the haptics 1 partially surround the optic by more than 180° of the circumference of the optic. For example, a single haptic can surround at least 110°, 120°, 130°, 140°, 150°, 160°, 170° up to 175° or 180° of the circumference of the optic or any range therebetween.

Figure 18B:
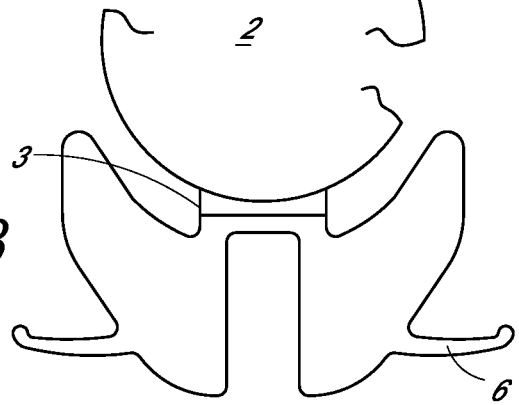
FIG. 18B illustrates one-half a lens with a haptic 1 having lateral members 30. The haptic 1 can be wider than the optic with finger-like flexible lateral extensions 6.

As shown in FIG. 18B, the haptics 1 can have lateral members (or paddles) 30 having distal arcuate outer edges becoming parallel to the longitudinal length proximally to the optic. The haptic 1 can be wider than the optic with finger-like flexible lateral extensions 6. The lateral members 30 can be connected by a short optic extension 3 across which is the rigidly flexed junction 4 between the optic 2 and the haptic 1. In some embodiments, the haptics 1 partially surround the optic by more than 180° of the circumference of the optic. For example, a single haptic can surround at least 110°, 120°, 130°, 140°, 150°, 160°, 170° up to 175° or 180° of the circumference of the optic or any range therebetween.

FIGS. 9A-9D illustrate a non-accommodating IOL comprising a flexible optic 2 with rigid haptics 1, comprising a chassis 104 with two longitudinal rigid struts/plates 30 from which extend two laterally extending closed loops 31, designed to both fixate and center the lens within the capsular bag. A distal bar 39 extends between the two struts/plates 30 creating a central enclosed open region 32. Accordingly, various embodiments may include one, two, three, four, or more closed loops 31 (and open regions 32) at least a portion of which may facilitate fixation via fibrosis. In some embodiments, the open regions 32 more central are larger than any open regions on either side of the central open region such as illustrated in FIGS. 9A-9D. The chassis 104 is partially embedded within the flexible material 43 of the optic. In various embodiments, the haptics 1 are biased with respect to the optic 2. Lines 107, which show the rigid flexed junction 4 in proximal portions of the frame or chassis 104 are indicative of the bias of the haptic 1 at an angle with respect to the optic 2 such as describe herein. In other embodiments, however, the design shown in FIGS. 9A-9D need not have the haptic biased with respect to the optic at the time of manufacture and thus need not include a rigid flexed junction 4 as shown. The cul-de-sac of the capsular bag 33 is shown partially distended to a radius of 11.5 mm.

Accommodating Lenses

Although certain embodiments have been described herein with respect to non-accommodating lenses, the haptics, potentially in combination with hinges or connecting bars can be used in accommodating lenses.

Various embodiments of haptics described herein including but not limited to those shown in FIGS. 6-9D can be used in accommodating lenses. Additional information regarding connecting bars and accommodating lenses can be found in U.S. patent application Ser. No. 14/035,821 published as U.S. Patent Publication No. 2014/0094909, filed Sep. 24, 2013 as well as U.S. patent application Ser. No. 14/035,813 published as U.S. Patent Publication No. 2015/0088254, filed Sep. 24, 2013, which are hereby incorporated by reference in their entirety and should be a considered a part of this specification.

FIGS. 14A-14D shows an example of an accommodating intraocular lens 200 having an optic 202 and opposing plate haptics 214. The plate haptic 214 can include a frame 222 embedded within a flexible component 226. The frame 222 can include through holes 230 through which the flexible component 226 can extend to secure the frame 222. The frame 222 can comprise polyimide, prolene, polymethylmethanylate (PMMA), titanium, or similar material. The flexible component 226 can comprise silicone, hydrogel, acrylic, or similar material. In some instances, the flexible component 226 and the optic 202 can be constructed from a same material such as for example acrylic.

Figure 14A:
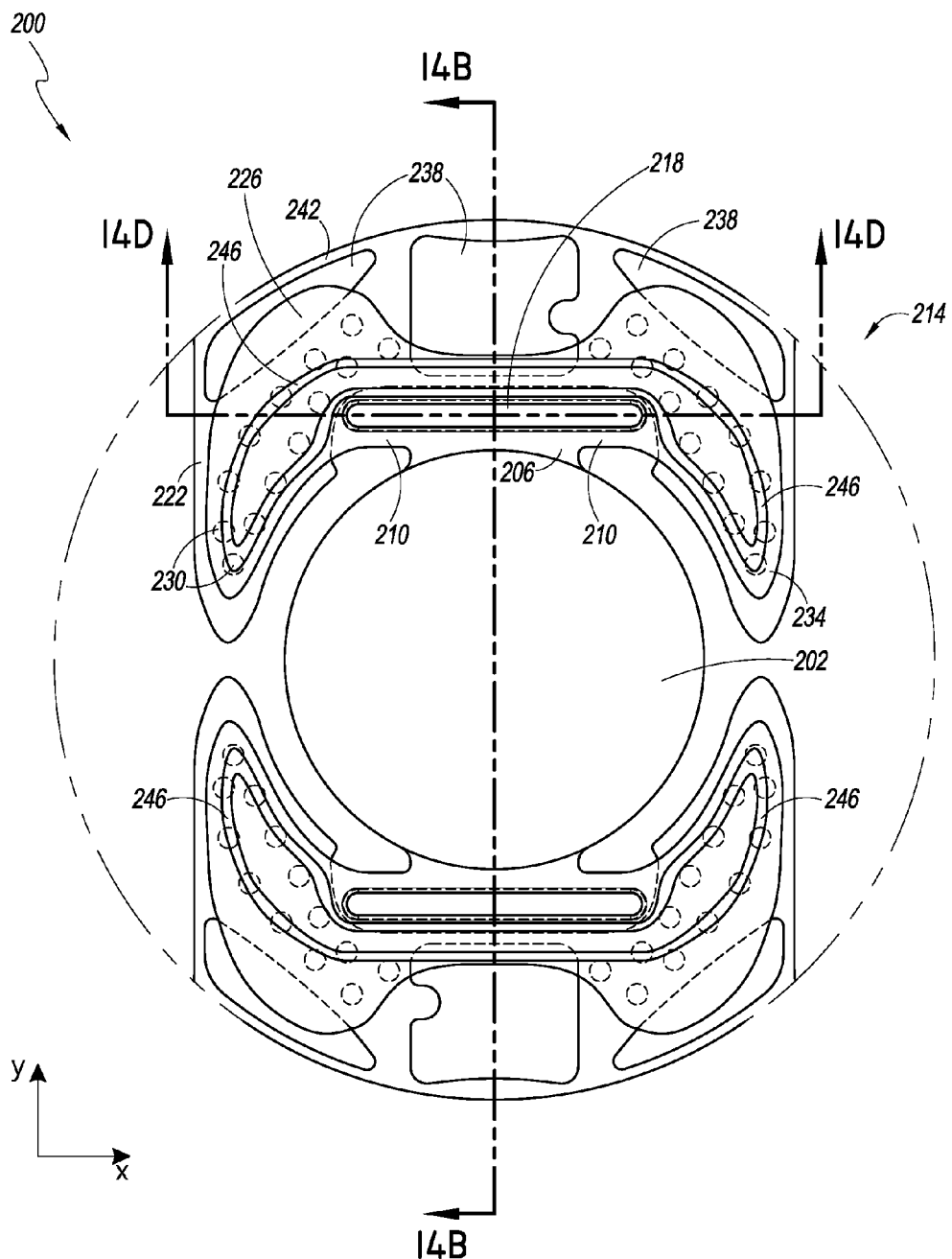
FIGS. 14A-14D illustrate a schematic diagram of an accommodating intraocular lens embodiment having a closed loop haptic.

As shown in FIG. 14A, the frame 222 can extend outwardly beyond proximal and distal edges of the flexible component 226. The exposed edges of the frame 222 reduce the slipperiness of the accommodating intraocular lens (AIOL) 200 during implantation to facilitate implantation in the correct position. The frame 222 can include a number of openings 238 (e.g., one, two, three, four, or more openings) at a distal portion thereof. At least some of the openings 238 can be at least partially formed by a thin, transverse bar 242 positioned at a distal end of the haptic 214. At least a portion of the openings 238 can extend beyond a distal edge of the flexible component 226, such that fibrosis can take place around the thin, transverse bar 242 and through the openings 238. Accordingly, as discussed above, various embodiments may include one, two, three, four, or more closed loops (and open regions 238) at least a portion of which may facilitate fixation via fibrosis. In some embodiments, the open regions 238 more central are larger than any open regions on either side of the central open region such as illustrated in FIGS. 14A-14D.

The plate haptic 214 can be constructed such that the plate haptic 214 can be substantially flexible in the transverse direction (e.g., parallel to the x axis) and substantially rigid in the longitudinal direction (e.g., parallel to the y axis). The plate haptic 214 can be sufficiently flexible to facilitate insertion of the AIOL into the eye, and be sufficiently rigid in the longitudinal direction to resist de-centration in response to ciliary muscle contraction, i.e. end-to-end compression.

A proximal portion of each plate haptic 214 can include opposing paddles 234 that at least partially surround the optic 202. In various embodiments, for example, a single haptic can surround at least 160°, 170° to 175° or 180° of the circumference of the optic or any range therebetween or possibly 110°, 120°, 130°, 140°, or 150° up to 160°, 170° or 180° of the circumference of the optic or any range therebetween. A transverse width measured between the outer lateral edges of the paddles 234 can be greater than a transverse diameter of the optic 202. The proximal portions of the paddles 234 can be spaced apart (e.g., disconnected) from the optic 202. Prior to implantation, the AIOL 202 can be manufactured substantially uniplanar. When the AIOL 200 is implanted in the eye, the optic 202 can vault posteriorly with respect to the distal end of the haptics such that at least the proximal portions of the paddles 234 lie posterior to the optic after implantation into the eye. When pushed posteriorly, the larger surface area of the paddles 234 can further increase pressure behind the AIOL 200, which can facilitate movement of the optic 202 in the anterior direction when the ciliary are constricted thereby increasing pressure of the fluid in the vitreous cavity.

Each of the opposing paddles 234 can include at least a portion of the frame 222 and at least a portion of the flexible component 226. The portion of the frame 222 forming the paddle 234 can be larger than the portion of the flexible component 226 forming the paddle 234. The portion of the frame 222 forming the paddle 234 can be wider and/or longer than the portion of the flexible component 226 forming the paddle 234. As shown in FIG. 14A, in the paddles 234, the frame 222 extends laterally beyond lateral edges of the flexible component 226 and proximally beyond a proximal edge of the flexible component 26.

Each plate haptic 214 can include a connection portion that can be connected to the optic 202. The connection portion can include a short appendage 206 and connecting bars 210 (e.g. torsion bars) extending laterally from the short appendage 206, e.g., a connecting bar 210 can extend laterally from each opposing lateral side of the short appendage 206. Each haptic 214 can include an elongate slot 218 forming a through hole that can be distal to the short appendage 206 and the connecting bars 210.

A thickness of the connecting bars 210 can be less than a thickness of the short appendage 206. The thickness of the connecting bars 210 can be reduced such that the connecting bars 210 can be stretched and/or rotated (e.g., twisted) to facilitate movement of the optic 202 relative to the haptics 214. Additional information regarding connecting bars and accommodating lenses can be found in U.S. patent application Ser. No. 14/035,821 published as U.S. Patent Publication No. 2014/0094909, filed Sep. 24, 2013, which is hereby incorporated by reference in its entirety and should be a considered a part of this specification.

Figure 14B:
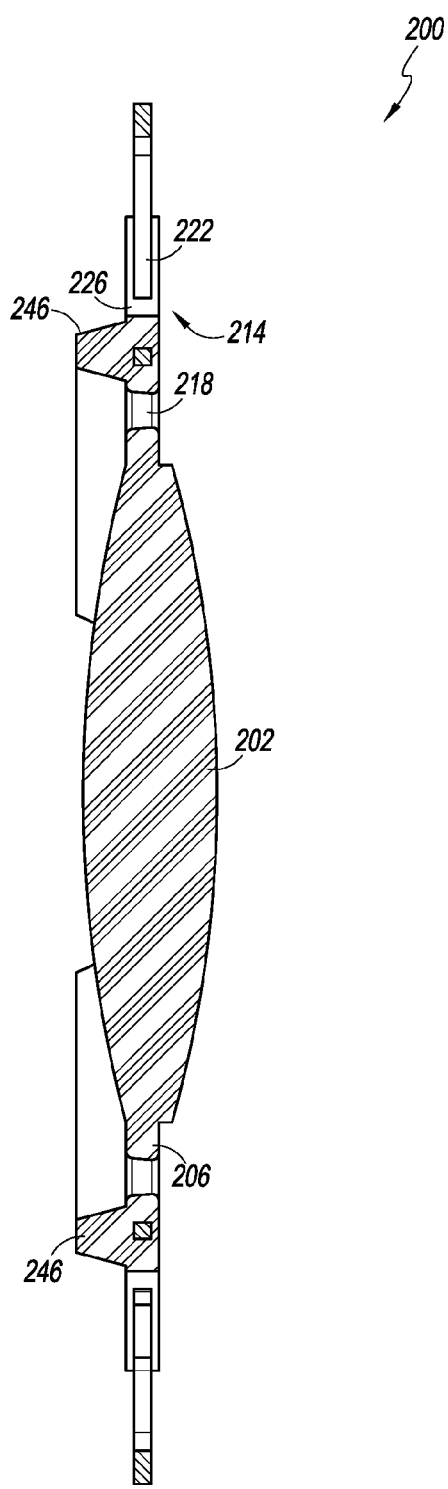
Figure 14C:
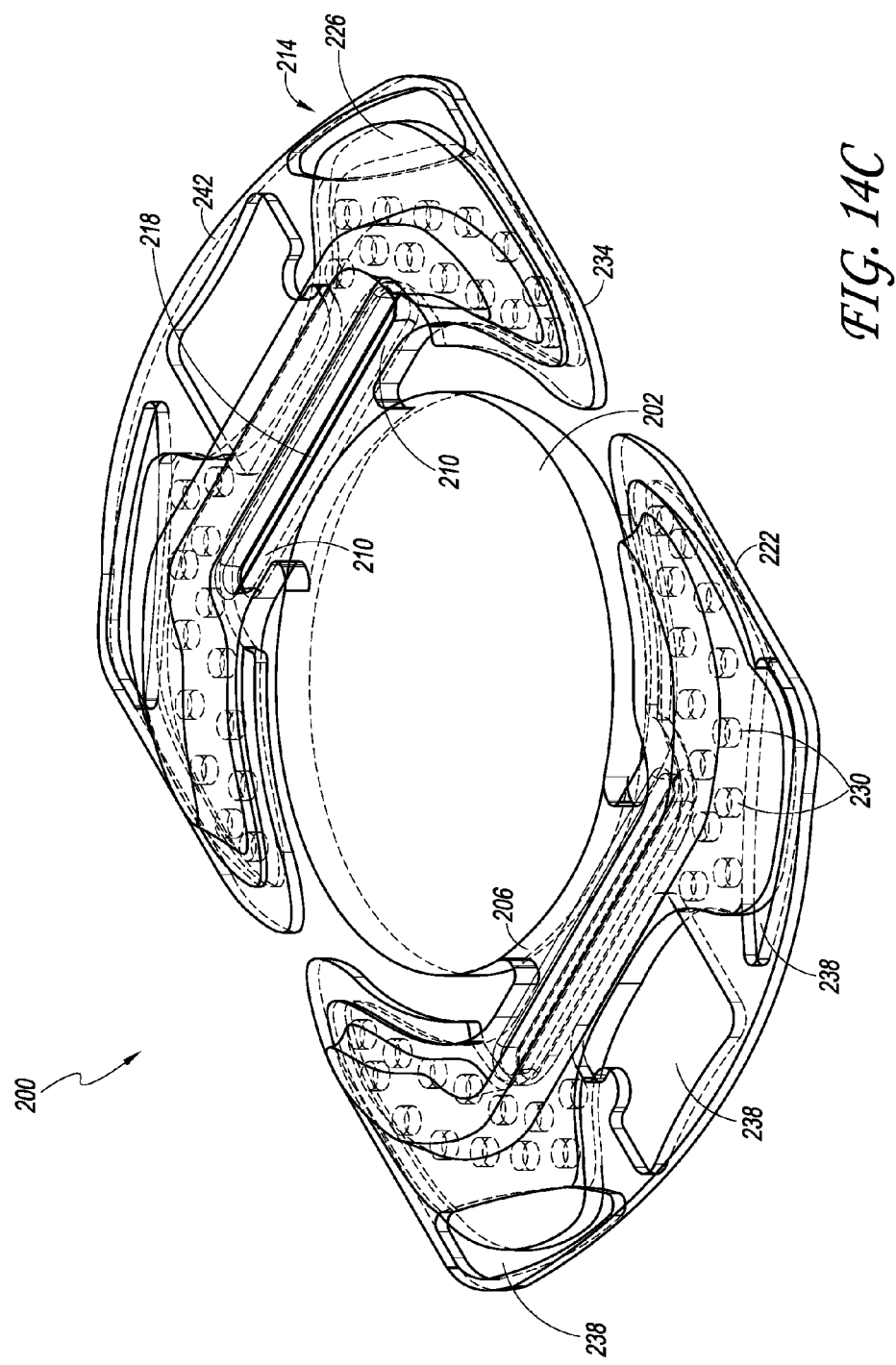
Figure 14D:

Each haptic 214 can include one or more anterior ridge protrusions 246 extending anteriorly from the haptic 214. Example ridge protrusions 246 are described in U.S. patent application Ser. No. 14/035,813 published as U.S. Patent Publication No. 2015/0088254, filed Sep. 24, 2013, which is incorporated herein by reference in its entirety and should be a considered a part of this specification. The one or more anterior ridge protrusions 246 can at least partially traverse the one or both paddles 234 of each haptic 214. As shown in FIG. 14A, a single anterior ridge protrusion 246 can extend from one paddle 234 to the other paddle 234 of the same haptic 214 and accordingly can be arcuate in the shape. In FIG. 14A, the light speckled portion of the haptic 214 is the frame 222, which may comprise polyimide. The darker area shows the portions where the flexible component 226 comprising, for example, silicone covers the frame 222. The darkest shaded areas show the ridge protrusion 246, which may comprise thicker regions of the flexible material comprising the flexible component 226 (e.g., silicone). In this configuration, the anterior ridge protrusion 246 can at least partially surround the elongate slot 218. Cross-sections of the ridge protrusion 246 are also depicted in FIGS. 14B and 14D. The one or more anterior ridge protrusions can separate the AIOL 202 from the anterior capsule of the human lens capsular bag. FIG. 14C shows the frame 222 (dark black area), which may comprise, for example, polyimide.

Such accommodating intraocular lenses can also have other features as described elsewhere herein.

TERMINOLOGY

As used herein, the relative terms "proximal" and "distal" shall be defined from the perspective of the optic. Thus, proximal refers to the direction toward the optic, and distal refers to the direction away from the optic.

As used herein, the terms "fixed length" or "fixed longitudinal length" refer to a change in length that is less than or equal to about 5% (e.g., less than or equal to about 4%, less than or equal to about 3%, less than or equal to about 2%, or less than or equal to about 1%) after implantation when subject to a force exerted by the ciliary muscle. For example, flexible fingers 5 may flex centrally to fixate the intraocular lens in the capsular bag (see FIG. 2). As used herein, the phrase "vault angle can remain unchanged" refers to a change that is less than or equal to about 5% (e.g., less than or equal to about 4%, less than or equal to about 3%, less than or equal to about 2%, or less than or equal to about 1%) after implantation when subject to a forces from the ciliary muscle and by fibrosis.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments, whether these features, elements, and/or steps are included or are to be performed in any particular embodiment.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 5% of the stated amount.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 3 mm" includes "3 mm."

Although certain embodiments and examples have been described herein, it will be understood by those skilled in the art that many aspects of the intraocular lenses shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A uniplanar intraocular lens comprising:
a lens optic;
a pair of opposing plate haptics flexibly coupled to the lens optic, each haptic comprising:
a flexible component, and
a longitudinally rigid frame at least partially embedded in said flexible component and extending beyond the distal edge of said flexible component, the rigidity of said frame being sufficient for the intraocular lens to be capable of resisting deformation by the pressure imposed by a ciliary muscle and by fibrosis without flexing such that the lens optic has the same location along the axis of the eye to maintain a fixed length of the intraocular lens,
said frame comprising a plurality of rigid loops located along its distal edge,
wherein said intraocular lens is longitudinally foldable, and
said lens optic being capable of vaulting posteriorly when said intraocular lens is implanted in an eye.

2. The intraocular lens of claim 1, wherein said loops are capable of permitting a capsular bag to fibrose around them to fix the location of the haptics within a capsular bag.

3. The intraocular lens of claim 1, comprising anterior ridge protrusion extending anteriorly from said haptic.

4. The intraocular lens of claim 3, wherein each plate haptic comprises two paddles which extend from said haptic laterally and proximally.

5. The intraocular lens of claim 1, comprising a connecting appendage extending distally from said lens optic.

6. The intraocular lens of claim 5, wherein said connecting appendage coupling at least one connecting bar extending laterally from the connecting appendage.

7. The intraocular lens of claim 6, wherein said haptic comprises a slot located distally and laterally from said connecting bars.

8. The intraocular lens of claim 7, wherein each plate haptic comprises two paddles which extend from said haptic laterally and proximally.

9. The intraocular lens of claim 1, wherein each plate haptic comprises two paddles which extend from said haptic laterally and proximally.

10. The intraocular lens of claim 9, wherein the haptics and paddles have a surface layer of silicone.

11. The intraocular lens of claim 1, wherein said loops are closed.

12. The intraocular lens of claim 11, wherein said loops are capable of permitting a capsular bag to fibrose around them to fix the location of the haptics within a capsular bag.

13. The intraocular lens of claim 11, comprising anterior ridge protrusion extending anteriorly from said haptic.

14. The intraocular lens of claim 11, comprising a connecting appendage coupling said lens optics to said haptics.

15. The intraocular lens of claim 11, wherein each plate haptic comprises two paddles which extend from said haptic laterally and proximally.

16. The intraocular lens of claim 11, wherein said intraocular lens is made entirely of acrylic.

17. The intraocular lens of claim 1, wherein said loops are open.

18. A monolithic uniplanar intraocular lens comprising:
a lens optic;
a pair of opposing plate haptics made from the same material as the lens optic wherein:
    said intraocular lens is longitudinally rigid, the rigidity being sufficient for the intraocular lens to resist deformation by the pressure imposed by the ciliary muscle and by fibrosis without flexing such that the lens optic has a fixed location along the axis of the eye to maintain a fixed length of the intraocular lens,
    said haptics comprising a plurality of rigid loops located along its distal edge, and
    a connecting appendage located between said lens optic and each of said haptics, said connecting appendage being coupled to at least one connecting bar,
    said lens optic being capable of vaulting posteriorly when said intraocular lens is implanted in an eye, and
    said intraocular lens being longitudinally foldable.

19. The intraocular lens of claim 18, wherein said connecting appendage at least one connecting bar extending laterally from the connecting appendage and coupling said lens optic to said haptics.

20. The intraocular lens of claim 19, wherein said haptic comprises a transverse slot located distally from said connecting bars.

21. The intraocular lens of claim 18, wherein said loops are closed.

22. The intraocular lens of claim 18, wherein said loops are open.

* * * * *